(12) United States Patent
Tepic et al.

(10) Patent No.: US 10,792,146 B2
(45) Date of Patent: Oct. 6, 2020

(54) HOLDING AND ADJUSTMENT MECHANISM FOR SURGICAL TETHER

(71) Applicant: KYON AG, Zurich (CH)

(72) Inventors: Slobodan Tepic, Zurich (CH); Daniel Martin, Palo Alto, CA (US)

(73) Assignee: Kyon AG, Zurich (CH)

(*) Notice: Subject to any disclaimer, the term of this patent is extended or adjusted under 35 U.S.C. 154(b) by 0 days.

(21) Appl. No.: 15/030,111

(22) PCT Filed: Oct. 24, 2014

(86) PCT No.: PCT/IB2014/003094
§ 371 (c)(1),
(2) Date: Apr. 18, 2016

(87) PCT Pub. No.: WO2015/059582
PCT Pub. Date: Apr. 30, 2015

(65) Prior Publication Data
US 2016/0354196 A1    Dec. 8, 2016

Related U.S. Application Data

(60) Provisional application No. 61/895,785, filed on Oct. 25, 2013.

(51) Int. Cl.
*A61B 17/04* (2006.01)
*A61F 2/08* (2006.01)

(52) U.S. Cl.
CPC ........ *A61F 2/0811* (2013.01); *A61B 17/0401* (2013.01); *A61B 2017/0403* (2013.01);
(Continued)

(58) Field of Classification Search
CPC ........ A61B 17/0401; A61B 2017/0403; A61B 2017/0408; A61B 2017/044;
(Continued)

(56) References Cited

U.S. PATENT DOCUMENTS 3,766,610 A   10/1973   Thorsbakken
4,510,934 A    4/1985   Batra
(Continued)

FOREIGN PATENT DOCUMENTS

EP   2623066      8/2013
EP   2623066 A1   8/2013
(Continued)

*Primary Examiner* — Melanie R Tyson
(74) *Attorney, Agent, or Firm* — Occhiuti & Rohlicek LLP (57) ABSTRACT

The present invention includes a device for engaging surgical tethers used in surgical repair, allowing for near full load application to the tether without failure at the site of restraint in the holding mechanism, with economical construction, compact size, and manageable complexity, without sharp edges that will cut the polymer fibers, and without requiring expensive polishing. The holding mechanisms comprise a tether, an orifice sheath, and a restraint element. The tether forms a bight projecting from the orifice sheath, the direction of projection being opposite to the direction of functional pull on the tether, where the bight is formed from a continuous tether or from coupled tether ends, and the restraint element is a fusiform structure positioned under the bight of the tether and over an orifice in the orifice sheath.

23 Claims, 3 Drawing Sheets

(52) U.S. Cl.
CPC . *A61B 2017/044* (2013.01); *A61B 2017/0445* (2013.01); *A61B 2017/0451* (2013.01); *A61B 2017/0458* (2013.01); *A61F 2002/0835* (2013.01); *A61F 2002/0852* (2013.01); *A61F 2002/0882* (2013.01)

(58) Field of Classification Search
CPC ..... A61B 2017/0445; A61B 2017/0458; A61F 2/0811; A61F 2002/0817; A61F 2002/0823; A61F 2002/0835; A61F 2002/0847; A61F 2002/0852; A61F 2002/0876; A61F 2002/0882
USPC ......................................................... 606/232
See application file for complete search history.

(56) References Cited

U.S. PATENT DOCUMENTS

| | | | |
|---|---|---|---|
| 4,656,806 A | 4/1987 | Leibhard et al. | |
| 4,898,505 A | 2/1990 | Froehlich | |
| 5,268,001 A * | 12/1993 | Nicholson | A61B 17/0401 606/104 |
| 5,336,240 A | 8/1994 | Metzler et al. | |
| 5,464,427 A | 7/1995 | Curtis et al. | |
| 5,480,403 A | 1/1996 | Lee et al. | |
| 5,571,139 A | 11/1996 | Jenkins, Jr. | |
| 5,575,819 A | 11/1996 | Amis | |
| 5,702,397 A | 12/1997 | Goble et al. | |
| 5,707,395 A | 1/1998 | Li | |
| 5,720,753 A | 2/1998 | Sander et al. | |
| 5,891,146 A | 4/1999 | Simon et al. | |
| 5,911,721 A | 6/1999 | Nicholson et al. | |
| 5,935,129 A | 8/1999 | McDevitt et al. | |
| 5,957,953 A | 9/1999 | Di Poto et al. | |
| 5,989,253 A | 11/1999 | Bigliardi | |
| 6,086,608 A | 7/2000 | Ek et al. | |
| 6,350,126 B1 | 2/2002 | Levisman | |
| 6,436,142 B1 | 8/2002 | Paes et al. | |
| 6,527,794 B1 | 3/2003 | McDevitt et al. | |
| 6,575,987 B2 | 6/2003 | Gellman et al. | |
| 6,585,730 B1 | 7/2003 | Foerster | |
| 6,616,694 B1 | 9/2003 | Hart | |
| 6,656,185 B2 | 12/2003 | Gleason et al. | |
| 6,923,824 B2 * | 8/2005 | Morgan | A61B 17/0401 606/232 |
| 7,083,638 B2 | 8/2006 | Foerster | |
| 7,090,690 B2 | 8/2006 | Foerster et al. | |
| 7,147,652 B2 | 12/2006 | Bonutti et al. | |
| 7,172,595 B1 | 2/2007 | Goble | |
| 7,217,279 B2 | 5/2007 | Reese | |
| 7,491,217 B1 | 2/2009 | Hendren et al. | |
| 7,828,820 B2 | 11/2010 | Stone et al. | |
| 7,976,565 B1 | 7/2011 | Meridew | |
| 8,133,258 B2 | 3/2012 | Foerster et al. | |
| 8,361,113 B2 | 1/2013 | Stone et al. | |
| 8,454,654 B2 | 6/2013 | Ferragamo et al. | |
| 8,523,902 B2 | 9/2013 | Heaven et al. | |
| 2002/0188298 A1 * | 12/2002 | Chan | A61F 2/0811 623/13.11 |
| 2003/0004545 A1 * | 1/2003 | Burkhart | A61B 17/0401 606/232 |
| 2003/0195563 A1 | 10/2003 | Foerster | |
| 2004/0127907 A1 | 7/2004 | Dakin et al. | |
| 2004/0267360 A1 | 12/2004 | Huber | |
| 2005/0209639 A1 | 9/2005 | Gidwani et al. | |
| 2005/0216058 A1 | 9/2005 | Egan et al. | |
| 2005/0288762 A1 | 12/2005 | Henderson et al. | |
| 2006/0116685 A1 | 6/2006 | Urbanski et al. | |
| 2006/0135996 A1 | 6/2006 | Schwartz et al. | |
| 2006/0149258 A1 | 7/2006 | Sousa | |
| 2006/0235413 A1 | 10/2006 | Denham et al. | |
| 2006/0247642 A1 | 11/2006 | Stone et al. | |
| 2006/0265010 A1 | 11/2006 | Paraschac et al. | |
| 2007/0038221 A1 | 2/2007 | Fine et al. | |
| 2007/0118217 A1 | 5/2007 | Brulez et al. | |
| 2007/0203498 A1 | 8/2007 | Gerber et al. | |
| 2007/0225719 A1 | 9/2007 | Stone et al. | |
| 2008/0234758 A1 | 9/2008 | Fisher et al. | |
| 2008/0249567 A1 | 10/2008 | Kaplan | |
| 2008/0288070 A1 | 11/2008 | Lo | |
| 2009/0012522 A1 | 1/2009 | Lob | |
| 2009/0234451 A1 * | 9/2009 | Manderson | A61B 17/8645 623/13.14 |
| 2009/0292321 A1 | 11/2009 | Collette | |
| 2010/0198258 A1 * | 8/2010 | Heaven | A61B 17/0401 606/232 |
| 2010/0318188 A1 | 12/2010 | Linares | |
| 2011/0046733 A1 | 2/2011 | Eggli | |
| 2011/0066185 A1 | 3/2011 | Wotton, III | |
| 2013/0345747 A1 * | 12/2013 | Dreyfuss | A61B 17/0401 606/232 |

FOREIGN PATENT DOCUMENTS

| | | |
|---|---|---|
| FR | 2683715 | 11/1991 |
| GB | 2084468 | 4/1982 |
| WO | WO 93/21857 | 11/1993 |
| WO | WO 95/00318 | 1/1995 |
| WO | WO95/15726 | 6/1995 |
| WO | WO 97/00766 | 1/1997 |
| WO | WO 02/17795 | 3/2002 |
| WO | WO2007/147634 | 12/2007 |
| WO | WO 2008/131370 | 10/2008 |
| WO | WO 2010/123835 | 10/2010 |
| WO | 2012145275 A2 | 10/2012 |
| WO | WO 2012/145275 | 10/2012 |

* cited by examiner

HOLDING AND ADJUSTMENT MECHANISM FOR SURGICAL TETHER

CROSS-REFERENCE TO RELATED APPLICATIONS

This application is a U.S. National Stage Application of International Application No. PCT/IB2014/003094, filed Oct. 24, 2014, which claims the benefit of the filing date of U.S. Application No. 61/895,785, filed Oct. 25, 2013. The content of each of these earlier-filed applications is incorporated herein by reference in its entirety.

FIELD OF THE INVENTION

The present invention relates to a holding mechanism for surgical tethers, which can be used in conjunction with devices such as bone anchors, for the repair and reconstruction of tissues such a ligaments. The holding mechanism can include a tether, an orifice sheath, and a restraint element. More particularly, the tether forms a bight projecting from the orifice sheath, the direction of projection being opposite to the direction of functional pull on the tether. The bight can be formed from a continuous tether or from coupled tether ends, and the restraint element is a structure, optionally fusiform in shape, positioned under the bight of the tether and over an orifice in the orifice sheath through which the tether passes.

BACKGROUND

Surgical tethers can be used to join tissues, to attach material to tissue, or to replace ligaments. Tissues may be joined, for example, to close wounds and/or to modify body structures. In some cases, lost or damaged ligaments may be replaced with a transplanted or artificial ligament by tethering the ligament to the bone. As an example, a procedure for replacing the anterior cruciate ligament (ACL) may comprise implanting two screws in bone that are coupled to a common artificial ligament.

SUMMARY OF THE INVENTION

The present invention features a holding mechanism for tethers, for example, surgical tethers that can be used to repair, reconstruct, or replace tissues, including damaged ligaments such as the ACL. The holding mechanism includes: a tether; an orifice sheath, which ensheaths a portion of the tether within a longitudinal passage having terminal ends that define first and second orifices of the orifice sheath; and a restraint element that restrains the tether. The orifice sheath may consist of or consist essentially of a tapered body; may consist of or consist essentially of a tapered body having a head (e.g., an enlarged head having a diameter or circumference that is larger than the diameter or circumference of the tapered body at the point the tapered body meets the head); or may comprise multiple components, including a tapered body and an insert that surrounds the terminal end defining the orifice nearest the restraint (i.e., a first orifice). The tether forms a bight projecting from the orifice sheath, with the bight projecting in a direction opposite from the direction of functional pull on the tether. As noted above, the bight can be formed from a portion of a continuous tether or from a portion of a discontinuous tether having coupled tether ends. By "continuous" we mean uninterrupted. The fibers within a continuous tether are not interrupted by apparent joins. At a gross level, a continuous tether is akin to a rubber band. In contrast, a "discontinuous" tether includes fibers that, prior to use, have two lose ends that, in use, are joined together. At a gross level, a discontinuous tether is akin to a shoe string, with an overall loop or looping structure formed when the two ends are tied to one another or otherwise joined at their ends.

The restraint element can be an elongated structure (e.g., fusiform structure) that, when in use, is positioned under the bight of the tether and over the first orifice. In some embodiments, the restraint element is fusiform in the region of the bight. As shown in FIG. 1, the holding mechanism can be used in concert with a bone anchor or bone screw, and devices including both a holding mechanism as described herein and a second structure, such as a bone anchor or bone screw, are also within the scope of the present invention. While we expect the holding mechanism to be supplied either assembled or within a kit for assembly (e.g., with tethers of variable lengths and/or with orifice sheaths of variable heights), the component parts (i.e., the tether, the orifice sheath, and the restraint element) can be used independently and are, independently or in any sub-combination, aspects of the present invention. Any of the holding mechanisms described herein can be packaged as a kit together with instructions for use. In one embodiment, the kit will include two or more orifice sheaths of the same or different heights, two or more tethers of the same or different lengths, and two or more restraint elements of the same or different configuration, as the methods of the invention can include the implantation of two holding mechanisms (e.g., one in a first bone and one in a second bone, with a tether between their facing ends). Accordingly, in another aspect, the invention features methods of joining tissues (e.g., generating or facilitating articulation between two bones or between a bone and a muscle) or attaching material to tissues. In one embodiment, the invention features methods of repairing, reconstructing, or replacing damaged ligaments.

The invention features a holding mechanism for surgical tethers that includes:
a tether; an orifice sheath comprising a longitudinal passage configured to accommodate the tether, the passage terminating in first and second orifices through which first and second portions of the tether protrude when the holding mechanism is deployed; and a restraint element. The tether forms a bight projecting from a first orifice of the orifice sheath and the restraint element is positioned under the bight of the tether and over the first orifice. The tether can be continuous or discontinuous in that it can include two ends. The bight can be formed by joining the two ends in any manner (e.g., by applying an adhesive or heat seal (heat fusion) or by tying or knotting). The tether can be a naturally occurring ligament (in which case it can be positioned adjacent bone to facilitate healing) or a prosthetic ligament. The tether can include fibers; the tether can include a polymer; and the tether can include an ultra high molecular weight polyethylene. The tether can be a monofilament or include a plurality of fibers (e.g., fibers or yarns arranged substantially parallel to one another or fibers that are interconnected (e.g., by braiding or weaving, by adhesion or heat fusion, or by tying or knotting). The tether can include a supplemental overlying structure (e.g., a tip as is applied in the process of tipping the ends of fibers). The orifice sheath can include an elongated body that is, optionally, conical along at least a portion of its length and has a rounded edge at the first orifice. For example, in some embodiments, the orifice sheath comprises a body, a head, and, optionally, an insert within the head that is of a different material than the orifice sheath. The rounded edge of the first orifice can have a radius of curvature of at least one time (e.g., about two times or less) of the diameter of the longitudinal passage. The orifice sheath can be comprised of plastic or metal or both plastic and metal and can have a shape to engage a surgical implant element (e.g., a bone anchor or bone screw). The restraint element can be fusiform in shape, particularly where it resides under the tether, and the restraint element can be a monofilament; comprise fibers; and/or comprises plastic. The holding mechanism can further include a retaining element (e.g., a ring or ring-like structure that is partially open) coupled to the restraint element to facilitate positioning or placement of the restraint element under the bight. The restraint element itself can also be a closed loop structure.

BRIEF DESCRIPTION OF THE DRAWINGS

In FIG. 1B, the tether is a continuous tether, with the bight being formed in a conventional manner by a loop in a portion of the tether. In FIG. 1C, the tether is a discontinuous tether, with the bight being formed by a join coupling (in this case, by a knot).

DETAILED DESCRIPTION

It is well known in the field of high tenacity textile fibers that manipulating and holding or securing these fibers is difficult, particularly under the stressful conditions that may occur in an operating room or under physiological peak or cyclic loading. Pinching and knotting the fibers can weaken them. Glues do not generally adhere well to such fibers. The fibers can also be so strong that adjacent materials cannot hold them because the adjacent materials are weaker than the fibers. The present invention includes devices for engaging these fibers, allowing for superior or near full load application to the tether without failure of the tether or holding mechanism. The holding mechanisms described herein may also offer other advantages, allowing for economical construction, compact size, and manageable complexity, and can be manufactured without sharp edges that will cut the fibers within the tether. With regard to economics, cost savings are envisaged where the tether is designed to tie around the restraint element because the surgeon can adjust the length of the tether during implantation, thus reducing the inventory that must be kept of tethers of varying lengths. The holding mechanism also allows for adjustment of tightness of a continuous (e.g., closed-loop) tether, eliminating the need for removal and discarding of wrong-length tethers. In addition, the restraint element can preclude the need for expensive metal polishing. In cases where closing means, such as knots, are used, the holding mechanism can reduce the localized tether weakness normally associated with the closing means.

An objective of the present invention is to maximally exploit the tensile strength of the tether used.

Figure 1A:
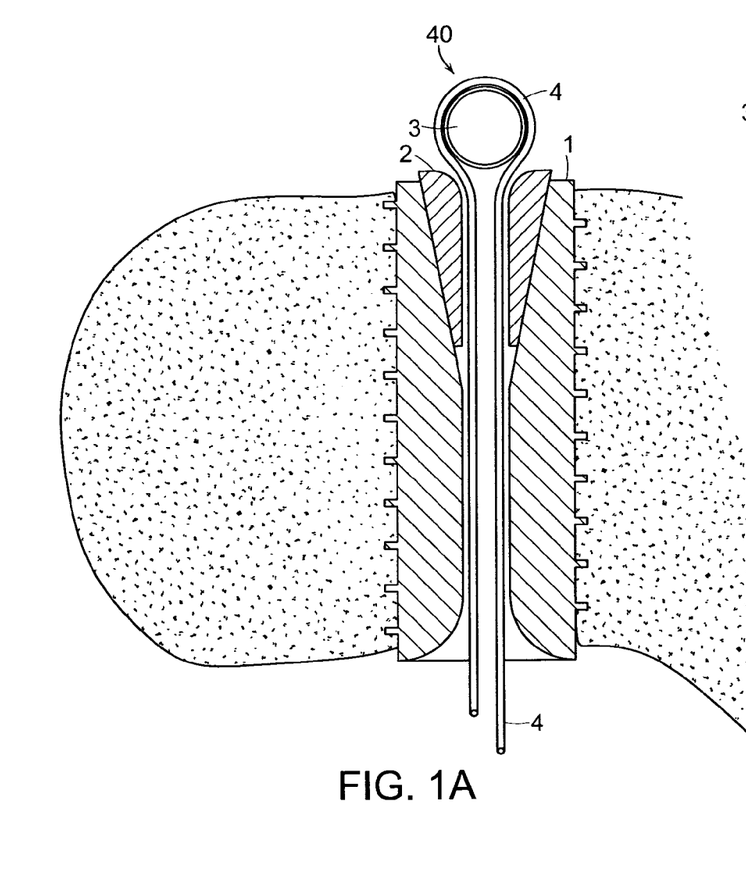
FIG. 1A is a schematic cross sectional view of a holding mechanism for a surgical tether within an orthopedic bone anchor situated in a bone.
Figure 1B:
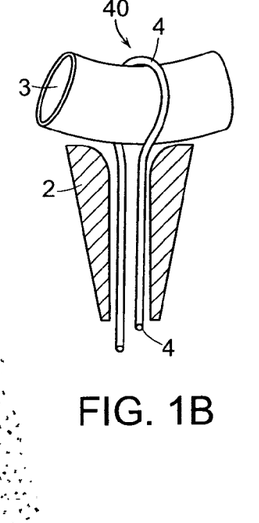
FIGS. 1B and 1C show the morphology of representative restraint elements.
Figure 1C:
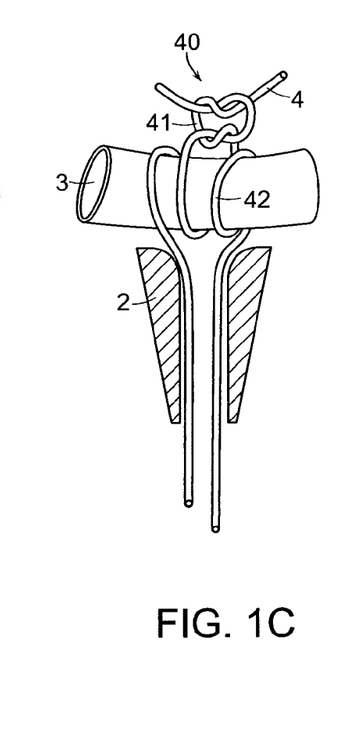

FIGS. 1A-1C illustrate embodiments of the present invention including a holding and adjustment mechanism for surgical tethers in the form of a tether 4, an orifice sheath 2, and a restraint element 3. The tether 4 forms a bight 40 projecting from the orifice sheath 2, the direction of projection being opposite to the direction of functional pull on the tether 4, where the bight 40 is formed from a continuous length of the tether or from ends of a tether (or tethers) that were originally discontinuous. The restraint element 3 is a fusiform structure shaped to allow positioning under the bight 40 of the tether 4 and over the first orifice in the orifice sheath 2, and the orifice sheath has a longitudinal passage for passage of the tether.

The load from the high tenacity tether 4 is transferred to the restraint element, without relying on adhesion between the tether 4 and the adjacent material, and without relying on compressive friction between adjacent fibers. The mechanism transfers load from the tether 4 to the restraint element 3 over a larger area than if the tether 4 were bearing against itself in a knot; this is achieved by increasing the cross-sectional area of the restraint element 3, to increase the radius of curvature of the tether 4 as it passes around the tether 4. This decreases the side-load pressure between the restraint element 3 and the tether 4. The cross-sectional area for load transfer can be adjusted according to application requirements.

The restraint element can be made of a material equal in tenacity to the tether. In this way, when the tether is loaded to ultimate strength, the restraint material will not fail before the tether. The restraint is preferably made of a mechanically anisotropic textile fiber, with the strong fiber substantially parallel to the long direction of the restraint element, passing under the tether's bight.

As a bulk structure, the restraint element is relatively soft, so that it conforms to the surface of the orifice and the tether as the tether is loaded. In this way, force transfer from the tether to the orifice is evenly distributed, avoiding localized peak loads. Further, the contact area between the restraint element and the orifice is typically much greater than the contact area between the tether and the restraint element. In this way, the material strength of the orifice can be less that that of the tether, allowing a plastic material such as PEEK to be used for the orifice. Use of a plastic material for the orifice reduces the surface treatment requirement for the orifice without risking having the orifice damage the tether fibers, and avoids expensive metal polishing steps. Use of a hard non-conforming material for the restraint element risks generating high peak loads between the restraint element and the orifice, pinching and cutting of tether fibers, progressive damage to the orifice, and debris generation.

A temporary restraint element may also be used temporarily during a surgical procedure. In these circumstances, the tether is tested for proper length, and ultimate strength is less important. It may be preferable to use a restraint element with a smooth surface, such as a nylon monofilament, that can easily be slipped under the tether bight while testing for length is done. The same temporary restraint element can then also be used to pull the permanent restraint element under the bight when proper tether length and tightness is ascertained.

The holding mechanism of the present invention achieves a tether failure strength that approaches the strength achieved when the tether 4 is wrapped around a smooth large cylinder; this represents the least possible weakening associated with a holding mechanism. Minimal weakening minimizes the thickness of the tether 4 required to achieve its intended function. The holding mechanism of the present invention optimizes function with a simple and reliable application technique.

FIGS. 1A-1C show three cross-sectional views of three embodiments of the holding mechanism of the present invention. In FIG. 1A the holding mechanism is shown positioned in an orthopedic bone anchor 1 implant.

In the embodiment of FIG. 1A, the bight 40 of the tether 4 extends continuously around the restraint element and lacks a join (such as a splice junction or coupling). FIG. 1B shows a perspective view of a continuous portion of a tether 4 forming a bight 40 around a restraint 3. In FIG. 1C, the bight 40 of the tether 4 is coupled and comprises two tether ends. In some embodiments, the bight 40 of the tether 4 is coupled with a knot 41. In some embodiments, the bight 40 of the tether 4 is wrapped around the restraint element 3 with extra revolution 42. Depending on the extent of the length adjustment required, the tether can be wrapped around the restraint once, twice, or three or more times before the ends are joined (e.g., coupled with a knot as shown in FIG. 1C). In FIGS. 1A-1C, the portion of the tether that is not drawn (i.e., the portion extending from the two ends shown at the bottom of the Figures) may be continuous (forming a bight in a second holding mechanism as shown in FIGS. 1A and 1B) or discontinuous (forming a bight in a second holding mechanism as shown in FIG. 1C).

As noted, the holding mechanism of the present invention allows the use of knots in the bight 40 of the tether 4, over the restraint element 3. This can be achieved by wrapping the tether 4 around the restraint element 3 before placing a bend-knot in the tether 4. The wrapping around causes a gradual decrease in tension in the tether as the tether approaches the location of the bend-knot. This takes advantage of the capstan principle. Each end may have three or less turns around the restraint element 3, in addition to the passage from the orifice hole to the far side of the restraint element 3.

The availability of holding mechanisms as described herein allows a medical facility to fully serve its patient population with a lower inventory of tethers, as the tether can be variously tied around a restraint and/or selected for use with an orifice sheath 2 of an appropriate height. The alternative of multiple closed loop tethers in different lengths is avoided. Alternatively, and as noted, the orifice sheaths of different heights may be used to adjust the tightness of a tether (e.g., a closed loop tether); this increases the step intervals required of the closed-loop lengths.

Use of a bend-knot adjacent to the restraint element 3 is advantageous because it allows a tether 4 that is not supplied as a closed loop. The tether may have two (or more) free ends. That configuration allows adjustment of the tether's length by choosing a variable placement position of a knot (or other joining) Some fibers of the bight may be coupled/spliced while other fibers (e.g., adjacent fibers) of the same bight are continuous (see FIG. 1C). Coupling may be from tangling of fibers, a so-called "air-splice," with a bend-knot, or with other means.

Figure 2:
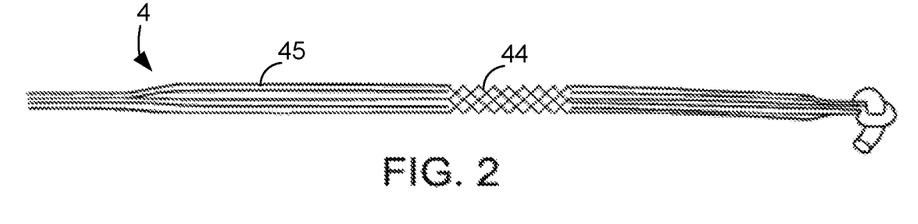
FIG. 2 shows a discontinuous tether (i.e., a tether with free ends) and illustrates two ways in which the fibers at the ends of the tether can be joined (i.e. by fusion as shown on the left-hand side and by knotting as shown on the right hand side). Along the length of the tether, the fibers can be substantially parallel or interconnected.

FIG. 2 shows one possible embodiment of a tether 4 and one or more of the features illustrated in that tether may be incorporated in other tethers useful in the context of the invention. For example, both ends of a discontinuous tether may include fibers that are either fused or knotted, and along the length of a continuous or discontinuous tether, the fibers can be arranged such that they are substantially parallel or interconnected (e.g., by weaving or braiding). The two free ends of a discontinuous tether can be part of a bight 40 when they are coupled together, for example with a bend-knot or other means. The tether 4 may also be formed from a structure that has been manufactured to form a substantially continuous loop as seen in FIG. 3B, where one end of the complete loop forms the bight 40 projecting from the orifice sheath 2. The tether 4 with two free ends is polyfilamentous, made of polymer, preferably UHMWPE (ultra high molecular weight polyethylene). It may consist of fibers lying parallel to one another 45, or braided together 44, or alternating zones along the length that are with alternating braided and parallel fibers. There may be knotting at the ends to hold the ends together, preventing dissociation of the parallel fibers near the ends. There may be a supplemental overlying structure at the ends holding parallel fibers together. The fibers may be adherent to one another in specific zones of the tether, by way of gluing or heat fusion, or bonding between the different fibers, or knotting at the ends. In some embodiments, the tether 4 is a prosthetic ligament. In some embodiments, the tether 4 is a prosthetic ACL ligament configured for joining bone to bone in a human patient or other mammal (e.g., a dog or cat).

The tether 4 is fabricated to offer optimal strength and durability offered by the fibers, and yet to allow practical application. Parallel fibers generally offer the greatest strength. Fibers that are connected together to form a cord are generally more easily handled by the surgeon. Tethers 4 that are with substantially parallel fibers, in the form of a closed loop, are claimed; this includes one or more yarn splices. The closed loop has no free ends that can be tied. This avoids all knots, with optimized restraint on both ends, but less convenient length adjustment.

Tethers 4 with substantially parallel fibers, including tethers having fibers joined at their free ends with knots, or by heat fusing, adhesive, braiding, or by collection within a overlying tubular structure, can be used with any of the restraints and orifice sheaths described herein. The joining of fibers at their ends preserves the fibers at an equal length between the ends and facilitates making intraoperative knots. This takes advantage of parallel fiber strength and the ease of handling of corded structure.

In case of coupling the tether 4 by way of a bend-knot, the knot may be found on the opposite side of the tether 4 from the orifice sheath 2. A bend-knot may be found after the orifice sheath 2 and before the arms of the tether 4 have passed more than ½ turn around the tether 4. Alternatively, the knot may be found after each arm of the bight 40 has passed one or more complete revolutions around the tether 4, before joining the other arm of the bight 40 and coupling by way of a bend-knot.

In the case of a splice by air entanglement or other means, the overlapping adjacent fibers of a splice may lie such that the zone of overlap is over the restraint element 3.

The splice refers to a connection where fibers from one end are tangled or wound between other fibers from an opposing end being coupled together. A knot is where the fibers of opposing coupled ends make turns greater than 180°. A bight 40 is where the tether makes a turn of approximately 180° without the tether crossing over itself. A loop is defined as a topological torus, and may be formed by coupling ends of a tether with two free ends, or a restraint element 3 with two free ends. It may also be formed by splicing.

Figure 3A:
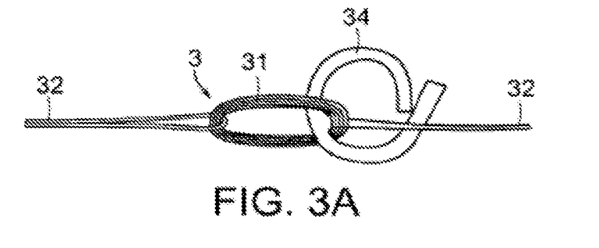
FIG. 3 shows various embodiments of the restraint element.
Figure 3B:
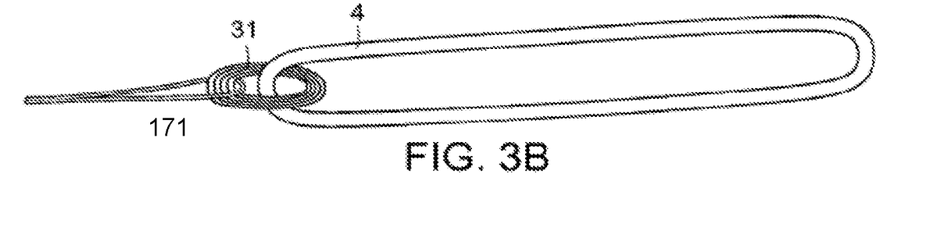

FIG. 3 illustrates multiple embodiments of the restraint element 3. FIG. 3A shows restraint element 3 comprising a coil of yarn 31 pulled into a fusiform shape with traction ties 32 positioned at opposite sides of the coil of yarn 31. In use, the coil of yarn 31 is stabilized by the two traction ties 32 passing through a central opening 33 of the coil of yarn 31, and each traction tie 32 passes around an opposing side of the opening 33 of the coil. In some embodiments, the ends of the traction ties 32 are tied together after the restraint element 3 is pulled under the bight 40, helping to hold the ends of the restraint element 3 together and in a fusiform shape, thereby stabilizing the restraint element in the desired position. We use the term "yarn" to mean a textile material, many of which are commercially available. In the context of the present invention, the yarn is preferably polyfilamentous but can be monofilamentous.

FIG. 3A also shows a monofilament ring 34 positioned through one end of the restraint element 3. The ring is preferably partially open to facilitate its removal after use. The ring 34 or analogous but differently shaped structures can be employed to prevent the restraint from being pulled too far under the bight. The ring 34 is preferably removed prior to completion of the surgery or at the conclusion of any other process in which the holding mechanism is assembled. The ring 34 may be made of metal, nylon, or other materials (e.g., it may be formed of a monofilament or may be polyfilamentous), and it may have a much greater length or different geometry than the ring illustrated here (e.g., it may be oval, square, rectangular, triangular, etc . . . ).

Where the restraint element 3 comprises fibers, the fibers can be oriented substantially longitudinally to the major axis of the restraint element 3. In some embodiments, the fibers of the restraint element 3 can be integrated with one another as a textile, such as a braided or woven textile, that may be coiled or otherwise arranged. In some embodiments, the fibers of the restraint element 3 are made of UHMWPE. In some embodiments, the restraint element 3 comprises a fibrous polymer material.

The restraint element 3 can be manufactured to have a material strength that is sufficiently great that it will not be damaged (e.g., cut) by the force of the tether bearing against it. In one embodiment, the restraint element 3 has at least the same material strength as the tether 4. For example, the restraint element 3 and the tether 4 can be fashioned from the same UHMWPE material. In some embodiments, the restraint element 3 can be fashioned from a lower strength material than the tether 4 if the cross-sectional area of the restraint element 3 is sufficiently high. In some embodiments, the restraint element and the tether are made wholly or partially from the same material or materials.

The cross-sectional area of the restraint element 3 plus the cross-sectional area of the tether 4 is greater than the cross section of the first orifice. Generally, dimensions are chosen where the cross section of the tether plus the cross section of the restraint is more than twice the cross-section of the orifice hole. More generally, regarding dimensions, the holding mechanism will be sized according to its intended use. For example, a holding mechanism intended for surgical repair, reconstruction, or replacement of a ligament will be sized such that the orifice sheath can fit within an implantable device, such as a bone anchor or bone screw (as illustrated in FIG. 1A) or such that the tether is appropriate in size to repair, reconstruct, or replace the damaged ligament.

FIG. 3B shows an embodiment in which the restraint element 3 is a coil of yarn 31 , and the tether 4 passes through an opening in the coil. In this case, the tether 4 is a continuous, closed loop tether, but the tether can also be discontinuous and/or have any of the other features and characteristics described herein. The coil of yarn 31 ultimately comes to rest against the first orifice when the tether loop is pulled with a traction tie 32 into the first orifice and through the orifice sheath.

Figures 3C, 3D:
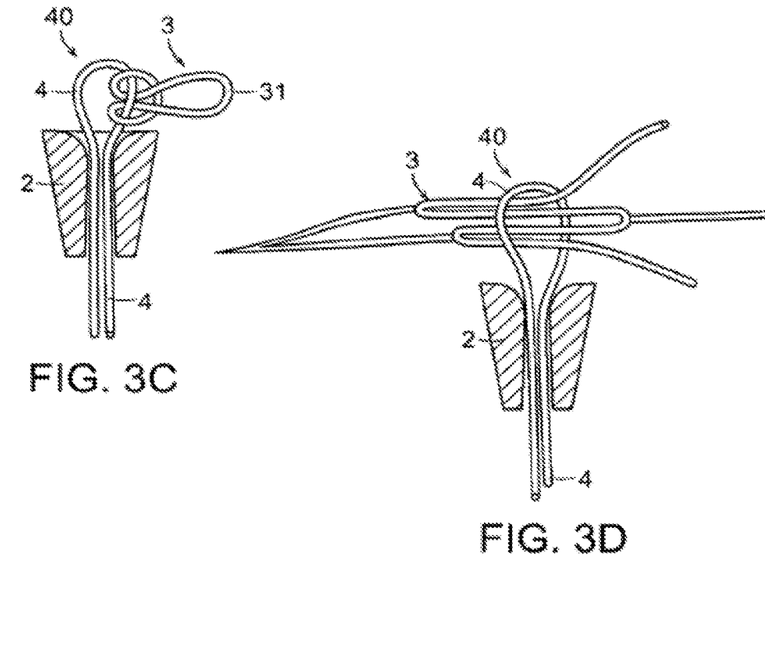

FIG. 3C shows a restraint element 3 made from a closed coil of yarn 31 that is thin enough and long enough to be looped through itself and secured to itself after it is passed under the bight 40. The restraint element can also be fashioned from a discontinuous length of yarn, another fusiform textile structure, or a plastic.

FIG. 3D shows an embodiment in which the cross-section of the restraint element 3 increases incrementally or stepwise as it is pulled with traction ties 32 under the bight. As drawing a flexible restraint into a bight can be difficult to achieve in one step, incrementally or progressively increasing the cross section in order to position the restraint within the bight may be preferable. In this embodiment, the restraint element can be made from a piece of braided cord of a selected thickness (e.g., the denier of the tether), but it may also be made using alternate methods including different sized coils of yarn. After this flexible restraint element is positioned under the bight, it may also be looped through itself to secure it, as in FIG. 3C.

Figure 4A:
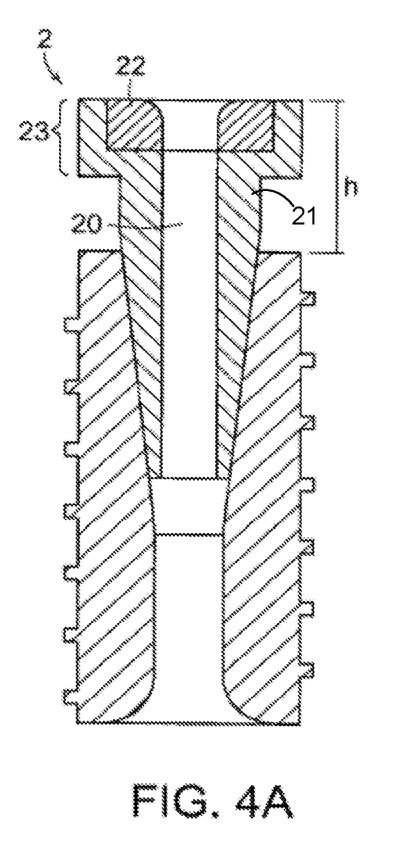
FIGS. 4A and 4B show embodiments of a holding mechanism in which the orifice sheath comprises a tapered body with a head. In the cross-sectional view of FIG. 4A, the head comprises a distinct insert surrounding the first orifice, and in FIG. 4B, the region occupied by the insert is integrated into the structure of the head of the orifice sheath. The length of the tether is adjusted by selecting an orifice sheath having a desired height, h, above the bone anchor.
Figure 4B:
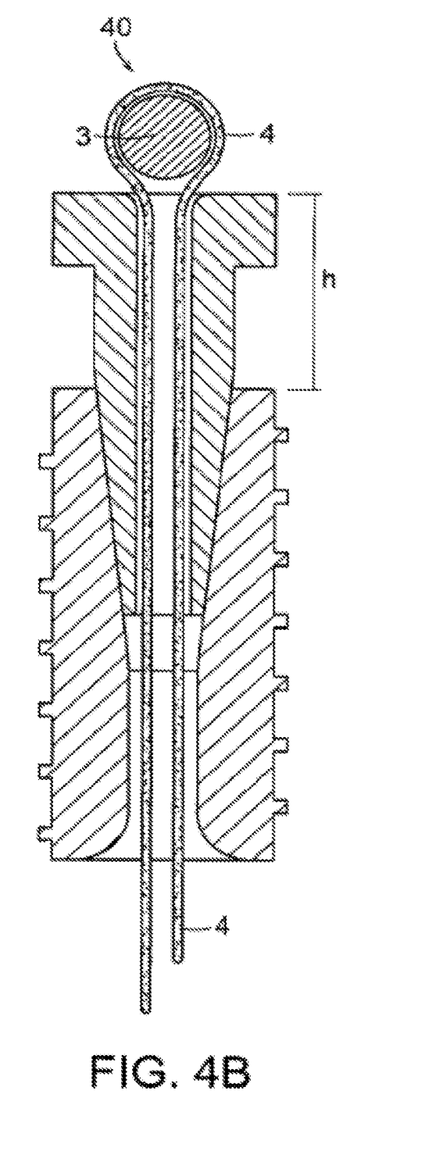

FIGS. 4A and 4B illustrate embodiments of a holding device in which the orifice sheath 2 facilitates adjustment of the length of the tether by virtue of the height h of the orifice sheath that extends beyond the structure that anchors the orifice sheath (in this illustration, a bone anchor 1). Where a closed loop tether is used, it is beneficial to be able to adjust the tightness of the tether without removing and replacing the tether with a tether of a different length. The orifice sheath can be manufactured in many different sizes (e.g., with variable height along the long axis) such that when a given orifice sheath is positioned within a device (e.g., a bone anchor or bone screw) the restraint and tether within it will be positioned at the desired height h above the end of the device. Generally, h varies in about 1 mm increments, and the kits of the invention can include a plurality of orifice sheaths varying in height by increments of about 0.5-1.0 mm. For example, if a surgeon placed a holding mechanism within a patient in the context of ligament replacement and determined that the tether (in this case, a tether serving as a prosthetic ligament) was too loose, the surgeon would remove the orifice sheath while leaving the tether in place, and then replace the orifice sheath with one having a greater height h. Using this technique, it is possible to vary the tightness of a tether by at least plus-or-minus 4 mm (e.g., by 0.5, 1, 2, 3, 4, or 5 mm).

The orifice sheaths, including those illustrated by FIGS. 4A and 4B, can be made entirely or primarily of metal, whereas the orifice sheaths illustrated by FIGS. 1A-1C may be made of PEEK plastic. There may be advantages to having the restraint element and tether bearing against PEEK plastic. For example, the use of this material can preclude a polishing step that may be necessary or advisable where metal is employed instead. The orifice sheath may be made of metal, and the insert 22, where present, may be made of plastic or metal. As noted, in one embodiment, the orifice sheath may include a portion that is shaped as an insert as an integral part of the orifice sheath. It is anticipated that a metal orifice will be made smooth to avoid abrasive damage to the tether.

After the load is transferred from the tether 4 to the restraint 3 and then to the orifice, the load may be transferred to the orifice 22 over a greater surface area, than if the load were transferred directly from the tether 4 to the orifice sheath 2. This allows the orifice portion of the orifice sheath 2 to be made of a material of lower ultimate strength than the tether 4 or restraint elements 3.

The orifice sheath 2 is preferably made of PEEK plastic or titanium metal alloy, but may be made of other plastics or metals. The plastic is not abrasive against the UHMWPE fiber, and sharp edges are easily avoided. Other materials also function, but require special surface treatments and likely greater expense. When the orifice is made of metal in contact with the restraint and the tether, the surface of the orifice is polished smooth. The orifice sheath may be made of metal and plastic, and the portion of the orifice sheath that is the orifice may be plastic.

The first orifice within the orifice sheath (i.e., the orifice residing nearest the restraint element) can have rounded edges. In some embodiments, the radius of curvature of the rounded edge will be equal to or less than about two times the diameter of the orifice hole. We use the term "about" to define a quantity that is plus-or-minus 10% of a referenced value. For example, "about" 10 mm means 9-11 mm. "About" two times the diameter of the orifice hole means 1.8-2.2 times the diameter of the orifice hole. Where a range is provided or implied (e.g., by using the term "about"), the range includes the end points. For example, a range of 9-11 mm encompasses an item that is 9 mm long, an item that is 11 mm long, and items that are between 9 and 11 mm long.

The orifice sheath 2 has a longitudinal passage 20 for the passage of both sides of tether 4, the orifice sheath 2 having a minimum cross-sectional area. The orifice sheath can be made of plastic or metal, preferably PEEK plastic. In some embodiments, at least a portion of the orifice sheath 2 (e.g., the portion that resides within the anchoring structure) is a conical shape with the tether-bight and restraint element 3 positioned at the wide end 21 of the cone. The edge of the orifice sheath 2, adjacent to the bight 40 (i.e., the first orifice nearest the restraint), can have a rounded edge. In some embodiments, the orifice sheath 2 is shaped to engage surgical implant elements such as a cylindrical anchor screw. Alternatively, the orifice sheath may be incorporated into the body of an orthopedic implant (e.g., a bone anchor or bone screw), and implants including an orifice sheath as described herein are within the scope of the present invention. As shown in FIG. 4A, the insert 22 can be a distinct but fitted element within the head 23 of the orifice sheath 2. Alternatively, as shown in FIG. 4B, the head can include a portion having a curved shape, the insert being essentially integrated into the head 23 of the orifice sheath 2.

What is claimed is:

1. A holding mechanism for surgical tethers, the holding mechanism comprising:
    a tether;
    an orifice sheath comprising a longitudinal passage defined in a conical-shaped body, the conical-shaped body having a wide end and a tapered narrow end, the orifice sheath accommodating a section of the tether, the passage terminating in first and second orifices through which first and second portions of the tether protrude, with the first orifice located at the wide end of the orifice sheath; and
    a restraint element with a soft elongated structure independent from the tether, the soft elongated structure of the restraint element being conformable to a surface of the first orifice;
    wherein another section of the tether forms a bight projecting from the first orifice of the orifice sheath, and wherein the soft elongated structure of the restraint element, independent from the tether, is positioned under the bight of the tether and over the first orifice located at the wide end of the conical-shaped body of the orifice sheath such that the soft elongated structure of the restraint element contacts the wide end of the conical-shaped body defining the first orifice and conforms to the surface of the first orifice without being received within the longitudinal passage defined in the conical shaped body of the orifice sheath.

2. The holding mechanism of claim 1, wherein the tether is continuous.

3. The holding mechanism of claim 1, wherein the tether comprises two ends.

4. The holding mechanism of claim 3, wherein the bight comprises a join of the two ends.

5. The holding mechanism of claim 4, wherein the join comprises a knot or an adhesive.

6. The holding mechanism of claim 1, wherein the tether is a prosthetic ligament.

7. The holding mechanism of claim 1, wherein the tether comprises fibers.

8. The holding mechanism of claim 7, wherein the fibers comprise a polymer.

9. The holding mechanism of claim 1, wherein the tether comprises fibers arranged substantially parallel to one another.

10. The holding mechanism of claim 1, wherein the tether comprises fibers that are interconnected.

11. The holding mechanism of claim 10, wherein the fibers are interconnected by braiding or weaving, by adhesion or heat fusion, or by knotting.

12. The holding mechanism of claim 1, wherein the tether comprises a supplemental overlying structure.

13. The holding mechanism of claim 1, wherein the orifice sheath has a rounded edge at the first orifice.

14. The holding mechanism of claim 13, wherein the rounded edge has a radius of curvature of about two times or less the diameter of the longitudinal passage.

15. The holding mechanism of claim 13, wherein the orifice sheath has a shape to engage a surgical implant element.

16. The holding mechanism of claim 15, wherein the surgical implant element is a bone anchor or bone screw.

17. The holding mechanism of claim 1, wherein the orifice sheath is comprised of plastic or metal or both plastic and metal.

18. The holding mechanism of claim 1, wherein the restraint element is fusiform in shape; is a monofilament; comprises fibers; and/or comprises plastic.

19. The holding mechanism of claim 1, wherein the holding mechanism further comprises a retaining element coupled to the restraint element to facilitate positioning or placement of the restraint element under the bight.

20. The holding mechanism of claim 1, further comprising a surgical implant element implantable into a bone, wherein the orifice sheath is fitted within the surgical implant element.

21. The holding mechanism of claim 1, wherein a cross-sectional area of the restraint element plus a cross-sectional area of the tether is more than twice a cross-sectional area of the first orifice.

22. The holding mechanism of claim 1, wherein the restraint element is a closed loop structure.

23. A holding mechanism for surgical tethers, the holding mechanism comprising:

a tether;

an orifice sheath comprising a longitudinal passage defined in a conical-shaped body, the conical-shaped body having a wide end and a tapered narrow end, the orifice sheath accommodating a section of the tether, the passage terminating in first and second orifices through which first and second portions of the tether protrude, with the first orifice located at the wide end of the orifice sheath; and a restraint element with an elongated closed loop structure independent from the tether;

wherein another section of the tether forms a bight projecting from the first orifice of the orifice sheath, and wherein the elongated closed loop structure of the restraint element, independent from the tether, is positioned under the bight of the tether and over the first orifice located at the wide end of the conical-shaped body of the orifice sheath such that the elongated closed loop structure of the restraint element contacts the wide end of the conical-shaped body defining the first orifice, without being received within the longitudinal passage defined in the conical shaped body of the orifice sheath.

* * * * *